United States Patent [19]
Esser et al.

[11] Patent Number: 5,940,177
[45] Date of Patent: Aug. 17, 1999

[54] METHOD AND APPARATUS FOR DETERMINING THE SIZE DISTRIBUTION OF DIFFERENT TYPES OF PARTICLES IN A SAMPLE

[75] Inventors: Anton Esser, Mannheim; Frank Runge, Mandorf; Hans-Peter Kaub, Altrip, all of Germany

[73] Assignee: BASF Aktiengesellschaft, Ludwigshafen, Germany

[21] Appl. No.: 09/004,341

[22] Filed: Jan. 8, 1998

[30] Foreign Application Priority Data

Jan. 10, 1997 [DE] Germany ............................ 197 00 648

[51] Int. Cl.[6] .................................................. G01N 21/00
[52] U.S. Cl. .......................... 356/338; 356/343; 356/39; 356/73
[58] Field of Search .................................. 356/335–343, 356/73, 39; 435/30, 34, 724; 436/10, 52

[56] References Cited

U.S. PATENT DOCUMENTS 3,710,933  1/1973  Fulwyler et al. ........................ 356/39
5,408,307  4/1995  Yamamoto et al. ..................... 356/73
5,486,904  1/1996  Horn et al. .............................. 356/73
5,757,476  5/1998  Nakamoto et al. ..................... 356/73

OTHER PUBLICATIONS

Wilken et al., *Mitt. aus dem Papier. Inst.*, vol. 11–12, 1984, pp. 292–307.

Kroehl et al., *Nordic Pulp and Paper Research Journal*, vol. 9, 1994, No. 1, pp. 26–30, 36.

*Primary Examiner*—Hoa Q. Pham
*Attorney, Agent, or Firm*—Keil & Weinkauf

[57] ABSTRACT

A method and apparatus for determining the size distribution of at least two different types of fluorescent or fluorescently stained particles in a sample by radiating light into a stream of singled particles and recording and analyzing both the scattered light and the fluorescent light. A relative particle size distribution for each individual particle type ($T_k$) is calculated and then the relative particle size distribution for the individual particle types is normalized forming a joint relative particle size distribution of the at least two particle types with respect to one another.

10 Claims, 7 Drawing Sheets

METHOD AND APPARATUS FOR DETERMINING THE SIZE DISTRIBUTION OF DIFFERENT TYPES OF PARTICLES IN A SAMPLE

The present invention relates to a method and an apparatus for determining the joint size distribution of particles of different types in a sample.

BACKGROUND OF THE INVENTION

1. Field of the Invention

In the field of papermaking, for example, aqueous suspensions are produced which contain contaminant particles of various types and sizes. These contaminant particles are often hydrophobic and sticky. They may lead to deposits in machinery which have to be removed during expensive down-time periods. Such deposits consist, for example, of poly(vinyl) acetate, polystyrene, polyacrylate, wax, paraffin wax, natural rubber or other substances which often originate from recycled adhesive tapes, hot-melt adhesive bridges, self-sealing envelopes or from coating waste or bituminized or waxed paper. To prevent such deposits, one option is to attempt to either filter out the contaminants or to precipitate them; alternatively, the pulp is admixed with chemical additives which bind the contaminant particles in finely dispersed form to the wood fibers in the pulp and thus prevent deposition in the machines. The quality and the economic efficiency of papermaking in this context depend on the choice of additive and how much of it is added. If the type, amount and size of the contaminant particles fluctuate, this has to be reflected in changes in the type and amount of the additive added. This in turn is only possible if the type, amount and size of the contaminant particles are known as accurately as possible. In this context it is particularly important to know the size distribution of the contaminant particles.

2. The Related Art

Conventional test methods, for example X-ray microanalysis, infrared spectrophotometry or gel permeation chromatography, as reviewed in R. Wilken and J. Strauss, "Grundlegende Untersuchungen über klebende Verunreinigungen im wiederverwendeten Altpapier" [Fundamental studies on sticky contaminants in reused wastepaper], Mitteilungen aus dem Papiertechnischen Institut der Papiertechnischen Stiftung, Vol. 11–12 (1984), p. 292 et seq. can be used to determine the type of contaminant particles, ie. their chemical composition, in the laboratory. Qualitative statements on the concentration and particle size distribution are also possible. All these methods have the drawback, however, that they are relatively time-consuming and laborious and are therefore unsuitable for direct monitoring of changes in contaminant and of the effect which additives have on the binding of the contaminants to the pulp during the production cycle.

A different method for determining the particle size distribution of contaminant particles is described in T. Kröhl, P. Lorencak, A. Gierulski, H. Eipel and D. Horn, "A new laser-optical method for counting colloidally dispersed pitch", Nordic Pulp and Paper Research Journal, Vol. 9 (1994), No. 1, p. 26 et seq. In this method, contaminant particles are singled by hydrodynamic focusing in a cell and are stained with a fluorescent dye. Laser light is then radiated into the sample containing the singled contaminant particles, and fluorescent light emitted by these is recorded. The particle size distribution can then be inferred from the intensity of the fluorescence signals. This method, though, will not provide a sufficiently precise particle size distribution unless the sample either contains only one particle type or contains a plurality of particle types which, however, have approximately equal stainability for the fluorescent dye used and comparable quantum yield. Since these prerequisites are rarely met in practice, the fluorescence-optical measuring method does not provide a procedure reliable in practice for determining the particle size distribution in a sample containing a number of different-type particles. A further drawback is that it is not possible to distinguish between a plurality of different particle types. Consequently, the additive cannot, in terms of type and quantity, be tailored to the conditions applying in each particular case.

Problems similar to those in papermaking also exist in many other industrial fields, in particular with recycling processes, where contaminants or alternatively valuable substances have to be identified as precisely as possible, so that their treatment can be defined appropriately.

BRIEF SUMMARY OF THE INVENTION

It is therefore an object of the present invention to provide a method and an apparatus for determining the size distribution of at least two different types of particle species in a sample. This object is achieved by the method described in the method claims and by the apparatus described in the apparatus claims.

DETAILED DESCRIPTION OF THE INVENTION

According to the invention, a method is provided for determining the size distribution of at least two particle types ($T_K$) of fluorescent particles ($P_i$) in a sample, fluorescent particles being particles which fluoresce naturally or after staining with a fluorescent dye. The method according to the invention comprises at least the following steps:

(a) First, the particles ($P_i$) in the sample are singled. This is preferably effected by hydrodynamic focusing of the particles. This involves a suspension of the particles to be studied being introduced continuously together with a water flow, the enveloping stream, into an enveloping-flow cell. The enveloping stream, which flows considerably more rapidly than the suspension, disperses the particles over a relatively long distance, so that the particles are eventually predominantly present as individual particles in the enveloping stream.

After the particles have been singled, light is shone into the sample in a predefined incident radiation direction. The light source used is preferably a laser.

(b) Then at least one scattered-light intensity value ($S(P_i)$) and at least one fluorescent-light intensity value ($F(P_i)$) is measured for each singled particle ($P_i$) moved past the light source, so that at least one pair of values ($S(P_i)$, $F(P_i)$) is obtained per particle ($P_i$). Depending on the extent to which random measuring errors are to be eliminated, it is also possible to determine a plurality of pairs of values per particle. Alternatively, of course, particles can just be studied randomly, if that be regarded as sufficiently informative. To measure the scattered light and the fluorescent light, appropriate detectors are located on the sample periphery.

The method according to the invention preferably involves recording the forward-scattered light of the sample, ie. the scattered light which is emitted from the sample in a cone around the incident radiation direction of the light. In so doing, the intense excitation light in the incident radiation direction is advantageously masked out. The scattered-light intensity values (S($P_i$)) are therefore preferably recorded in a hollow cone, whose inner lateral surface encloses an angle of at least 5° in the incident radiation direction, and whose outer lateral shell encloses an angle of at most 50° in the incident radiation direction.

To refine the measuring method, the scattered-light measuring cone can alternatively be subdivided into a plurality of cone layers, ie. angle segments, which are then analyzed separately. Additionally it is also possible to record and analyze a backscatter signal or a 90° scattering signal.

(c) In the next step, particles ($P_i$) are each, on the basis of the location of their pairs of values (S($P_i$), F($P_i$)) within a domain ($D_K$) in a three-dimensional space (Sp) spanned by the scattered-light intensity values (S($P_i$)), the fluorescent-light intensity values (F($P_i$)) and the frequency of the pairs of values (S($P_i$), F($P_i$)), assigned to a particle type ($T_K$), each domain ($D_K$) being defined so as to contain at least one local maximum for the frequency of the pairs of values (S($P_i$), F($P_i$)) for a particle type ($T_K$). This distinction between the different particle types ($T_K$) is possible for the first time in the method according to the invention, since this exploits the fact that the intensity of the scattered light and the fluorescent light depend in different ways on the particle type. A plot of the scattered-light intensity against the corresponding fluorescent-light intensity data therefore as a rule produces clearly distinguishable ranges of measured values, ie. a local frequency maximum of the pairs of values for scattering and fluorescence, a range corresponding to a particular particle type. From the location of the experimental point (S($P_j$), F($P_j$)) for a particular particle ($P_j$) in a particular domain of experimental points it is therefore possible to determine its particle type.

(d) Then the relative frequency of the fluorescent-light intensity values (F($P_i$)) is determined, from which the relative particle size distribution for each particle type ($T_K$) is calculated. If desired, a calibration in terms of absolute particle sizes can be carried out even at this stage, although this does presuppose knowledge with respect to a calibration factor specific for each particle type. After identification of the particles this can be done relatively easily since, once the particle types have been separated, the troublesome effects of the different stainability and unequal quantum yields of the various particle types have been eliminated at the same time. It is these differences, however, which in conventional methods do not allow a joint size distribution for all the particle types present in the sample to be inferred from the relative particle size distributions for the different particle types.

(e) Then the relative particle size distributions for the individual particle types ($T_K$) are normalized with respect to one another with the aid of the location of the domains ($D_k$) in the three-dimensional space (Sp) spanned by the scattered-light intensity values (S($P_i$)), the fluorescent-light intensity values (F($P_i$)) and the frequency of the pairs of values (S($P_i$), F($P_i$)). This is used to form a joint relative particle size distribution of all particle types ($T_K$). The normalization can in principle be carried out by any method, as long as the physical conditions are properly addressed.

Preferably, however, the following further steps are carried out to obtain said joint particle size distribution:

(a) A scattered-light range (SLR($T_K$)) of scattered-light intensity values (S($P_i$)) for each particle type ($T_K$) is selected which is of predetermined size and in which the frequency of the pairs of values (S($P_i$),F($P_i$)) of the particle type ($T_K$) has at least one local maximum and therefore the density of the experimental values is also at a maximum at least locally.

In so doing, the determination of the range of the highest experimental-value density or experimental-value frequency can be effected with the aid of a suitable algorithm, expediently in a computer, which has access to the pairs of values, or alternatively a visual optical estimate is possible on a monitor on which the scattered-light intensity values S($P_i$) are plotted against the fluorescent-light intensity values (F($P_i$)). The size of the range is defined beforehand, for example as a few percent of the scattered-light intensity value (S($P_i$)) which roughly represents the center of the range of maximum experimental-value density. Ultimately, the selected range simply has to be large enough to permit the mean to be calculated reliably by determining enough pairs of values, and small enough to minimize the effect of random measuring errors.

(b) When a scattered-light range (SLR) of scattered-light intensity values (S($P_i$)) of predetermined size having an upper and a lower range limit is determined, whose mean of the upper and the lower range limit equals the mean of the means of the scattered-light intensity values (S($P_i$)) in the respective scattered-light ranges (SLR($T_K$)). The scattered-light range (SLR) determined at this point comprises, for the various experimental-value ranges, ie. particle types, the ranges of highest or at least very high experimental-value density. This scattered-light range, which is standardized for all particle types, has to be determined for the fluorescence signals of the various particle types to be normalized with respect to one another, ie. for a measure to be available of the different stainability and quantum yield of the particle types. In many cases, the scattered-light ranges of greatest experimental-value density (SLR($T_K$)) for the individual particle types ($T_K$) will already largely coincide and thus form the joint scattered-light range (SLR). The size of the latter, ie. the range of scattered-light intensity values (S($P_i$)) spanned thereby, is predetermined. The above observations on the scattered-light ranges (SLR($T_K$)) apply correspondingly.

Instead of the relatively precise steps (a) and (b) being taken, the scattered-light range (SLR) can also simply be selected directly, without scattered-light ranges (SLR($T_K$)) being selected beforehand for the individual particle types ($T_K$) and mean values being calculated for scattered light therefrom. In this case an estimate is made of what experimental-value range the scattered-light range (SLR) roughly has to cover so as to include the points of greatest experimental-value density for all the different particle types ($T_K$). In so doing it is possible to adopt a procedure of greater or lesser precision, depending on how precise subsequent normalization is required to be, and even to select a scattered-light range (SLR) which in fact does not contain, for one or more particle types, the point of greatest experimental-value density.

(c) In the next step, one fluorescent-like range (FLR($T_K$)) each of fluorescent-light intensity values (F($P_i$)) is determined for each particle type ($T_K$) of predefined size, whose pairs of values (S($P_i$),F($P_i$)) likewise fall into the scattered-light range (SLR). Here, the fluorescent-light intensity values (F($P_i$)) associated with the scattered-light intensity values (S($P_i$)) in the scattered-light range (SLR) are determined for each particle type ($T_K$) ie. for each experimental-value range.

(d) Then the mean (M(FLR($T_K$))) of the fluorescent-light intensity values (F($P_i$)) is determined in the respective fluorescent-light range (FLR($T_K$)) for each particle type ($T_K$)

(e) Thence, for each particle type ($T_K$) a normalization factor (N($T_K$)) is calculated relative to a particle type ($T_1$)

chosen at will, the following relationship applying: $(N(T_K))=(M(FLR(T_K)))/(M(FLR(T_1)))$.

(f) As the last step, the relative particle size distributions of the particle types ($T_K$) are correlated to one another with the aid of the normalization factors ($N(T_K)$). Thus a joint particle size distribution for all the particle types ($T_K$) present in the sample has been obtained from the mutually incomparable relative size distributions of the different particle types ($T_K$). If the relationship between fluorescence intensity signal and absolute particle size is known for a specific particle type present in the sample under investigation it is thence also possible to obtain an absolute particle size distribution. This knowledge can be used, in the above example of papermaking, for selecting and proportioning an additive for binding finely dispersed contaminants to the pulp.

In a preferred embodiment of the method according to the invention, those pairs of values ($S(P_i)$, $F(P_i)$) in the scattered-light range (SLR) are excluded from the analysis which deviate from the respective mean ($M(FLR(T_K))$) by more than a degree of deviation predefined for each particle type ($T_K$). This elimination of presumed or actual wrong measurements can in principle take place at any stage of the method, but preferably when the particles ($P_i$) are assigned to a particular particle type. If it is found in the process that the pair of values ($S(P_j),F(P_j)$) of a specific particle ($P_j$) is clearly outside any distinguishable experimental-value range, it is expediently eliminated from further analysis. As a result, random errors in the measurements of scattered light and fluorescent light can propagate only to a limited extent into the normalization factors ($N(T_K)$). What deviation is considered acceptable for a particular experimental-value range, ie. a particular particle type ($T_K$), depends on the circumstances of each individual case, in particular on how precisely the random errors can be estimated and with what precision it is possible to decide, accordingly, whether an experimental value is erroneous or not.

Preferably, the method according to the invention is applied to hydrophobic contaminant particles ($P_i$). These contaminant particles are obtained, for example, by a pulp or wire water sample being drawn from a paper machine and the free contaminant particles being separated therefrom by filtration. The hydrophobic contaminant particles thus obtained are then stained with a preferably lipophilic fluorescent dye, are singled in a medium such as water and are studied optically as described.

Within the scope of the method according to the invention, the particles ($P_i$) may be stained with a plurality of different fluorescent dyes, the various dyes emitting fluorescent light in various wavelength ranges, which is recorded by a detector for each fluorescence band. These dyes can then be excitable either with the same excitation frequencies but only with different ones. In the latter case, light sources having correspondingly different frequencies are then used, the focal points of the light sources then either having to overlap or having to be close together, to ensure that the various recorded fluorescence signals indeed originate from the same individual particles. It is thus possible, with the aid of different fluorescence frequencies, for the particle types ($T_K$) still to be reliably distinguished from one another.

In addition to the methods described an apparatus is also provided, within the scope of the invention, for determining the size distribution of at least two types ($T_K$) of fluorescent singled particles ($P_i$) in a sample. This apparatus has at least one light source, for example a laser, which transmits a focused light beam along an incident radiation axis into the sample, the focus of the light beam preferably being within the sample, at least one means for recording at least one scattered-light intensity value ($S(P_i)$) for each particle ($P_i$), at least one means for recording at least one fluorescent-light intensity value ($F(P_i)$) for each particle ($P_i$), and an analysis unit which receives the scattered-light intensity values ($S(P_i)$) and the fluorescent-light intensity values ($F(P_i)$) for each particle ($P_i$) and which is designed so as to be able to carry out at least the following analysis steps:

(a) assignment of the particles ($P_i$) to a particle type ($T_K$) with the aid of the location of their pairs of values ($S(P_i)$, $F(P_i)$) within a domain ($D_K$) in a three-dimensional space (Sp) spanned by the scattered-light intensity values ($S(P_i)$), the fluorescent-light intensity values ($F(P_i)$) and the frequency of the pairs of values ($S(P_i)$, $F(P_i)$), each domain ($D_K$) having at least one local maximum of the frequency of the pairs of values ($S(P_i)$, $F(P_i)$) in the space (Sp) for the particle type ($T_K$);

(b) determination of the relative frequency of the fluorescent-light intensity values ($F(P_i)$) for each particle type ($T_K$);

(c) calculation of the relative particle size distribution for each particle type ($T_K$) from the relative frequency of the fluorescent-light intensity values ($F(P_i)$) for the respective particle type ($T_K$);

(d) normalization of the relative particle size distributions for the individual particle types ($T_K$) with the aid of the relative location of the domains ($H_K$) within the three-dimensional space (Sp) spanned by the scattered-light intensity values ($S(P_i)$), the fluorescent-light intensity values ($F(P_i)$) and the frequency of the pairs of values ($S(P_i)$, $F(P_i)$), with respect to one another; and (e) formation of a joint relative particle size distribution for all the particle types ($T_K$).

Preference is given to an apparatus having an analysis unit (23, 24, 25) which, to normalize the relative particle size distributions for the individual particle types ($T_K$) with respect to one another in step (d), is additionally able to carry out at least the following steps:

(a) selecting a scattered-light range ($SLR(T_K)$) of scattered-light intensity values ($S(P_i)$) of a predetermined size for each particle type ($T_K$), in which the frequency of the pairs of values ($S(P_i)$, $F(P_i)$) of the particle type ($T_K$) has at least one local maximum, (b) determining a scattered-light range (SLR) of scattered-light intensity values ($S(P_i)$) of predetermined size having an upper and a lower range limit, whose mean of the upper and the lower range limit equals the mean of the means of the scattered-light intensity values ($S(P_i)$) in the respective scattered-light ranges ($SLR(T_K)$). As already described in the process above, steps (a) and (b) can be replaced by a single step in which a scattered-light range (SLR) is selected without prior determination of the scattered-light ranges ($SLR(T_K)$) specific for each particle type. Here, the above comments apply to the selection of size and location of the scattered-light range (SLR), (c) determining a fluorescent-light range ($FLR(T_K)$) of fluorescent-light intensity values ($F(P_i)$) of predetermined size for each particle type ($T_K$) whose pairs of values ($S(P_i)$, $F(P_i)$) likewise are within the scattered-light range (SLR);

(d) determining the mean ($M(FLR(T_K))$) of the fluorescent-light intensity values ($F(P_i)$) within the fluorescent-light range ($FLR(T_K)$) for each particle type ($T_K$);

(e) forming a normalization factor ($N(T_K)$) for each particle type ($T_K$), relative to a particle type ($T_1$) chosen at will, the following relationship applying: ($N(T_K)$)=(M(FLR ($T_K$)))/(M(FLR($T_1$))); and (f) correlating the relative particle size distributions of the particle types ($T_K$) to one another with the aid of the normalization factors ($N(T_K)$).

The explanations given above for the corresponding steps of the process according to the invention apply analogously.

Preferably, the means for recording at least one scattered-light intensity value ($S(P_i)$) for each particle ($P_i$) is of such design and arrangement in the apparatus that the scattered-light intensity values ($S(P_i)$) are recorded in a hollow cone, whose inner lateral surface encloses an angle of at least 5° with the incident radiation axis of the light source (10), and whose outer lateral shell encloses an angle of at most 50° with that axis.

Preference is also given to an apparatus having an analysis unit which excludes those pairs of values ($S(T_i)$, $F(T_i)$) in the scattered-light range (SLR) from the analysis which deviate from the respective mean ($M(FLR(T_K))$) by more than a degree of deviation predefined for each particle type ($T_K$). What deviation in this context is regarded as tolerable, ie. as probably not based on measuring error, depends on the circumstances in each individual case. In this respect reference should again be made to the relevant explanations regarding the method.

The above novel method and the described apparatus are preferably suitable for determining the particle size distribution of particles in papermaking, in particular of contaminant particles, especially hydrophobic contaminant particles, in the pulp or in the wire water of paper machines. In particular they can be used for regulating or controlling the admixture of additives to pulp or wire water of paper machines, in particular of the type of additives which serve to render hydrophobic contaminant particles innocuous, in order to avoid deposits in paper machines. Said regulation or control is based on a control signal which is output as a result of the joint relative particle size distribution for the various contaminant particles. If relatively large particles are detected, a pump or a valve, for example, may add more or different additives. Thus it is possible for product quality to be maintained while the composition of contaminants is fluctuating.

BRIEF DESCRIPTION OF THE DRAWINGS

The present invention is described below with reference to FIGS. 1 to 5, in which.

DETAILED DESCRIPTION OF THE DRAWING AND EXAMPLE

Figure 1:
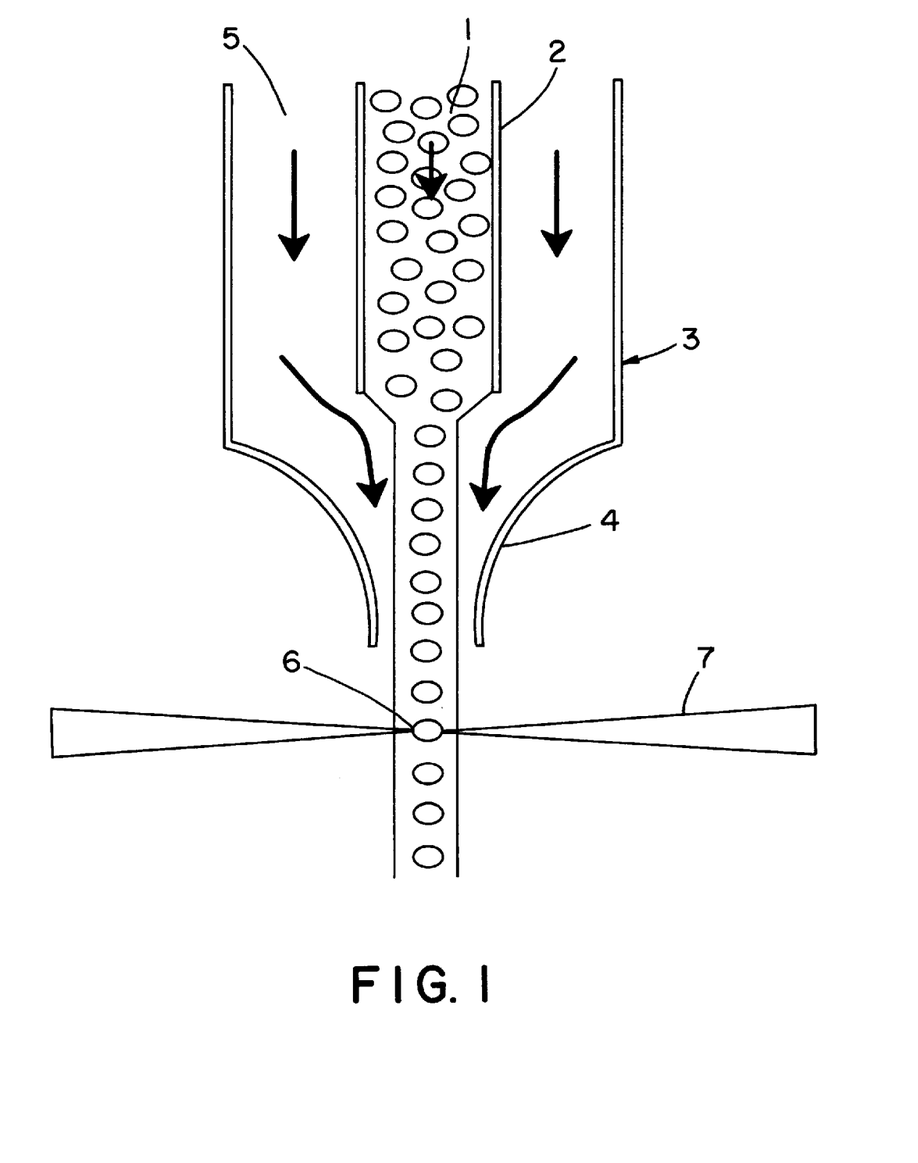
FIG. 1: shows a schematic representation of an apparatus for singling particles in a sample.

FIG. 1 shows an apparatus for singling particles in a sample. Singling of the particles to be studied optically is necessary within the context of the present invention to ensure that each individual experimental value, ie. each pair of values ($S(P_i)$,$F(P_i)$) pertains to a particular particle $P_i$. Thus it is possible, within the context of the method of the present invention, to estimate and eliminate the effects of different stainabilities and quantum yields. In the apparatus according to FIG. 1, a sample stream 1 containing the particles to be studied is passed through a capillary 2 into an enveloping-flow cell 3 which at its end has a nozzle 4. Via a hollow-cylindrical conduit 5, which surrounds the capillary 2, an enveloping flow, for example simply water, is introduced into the cell 3, the enveloping flow from the conduit 5 having a distinctly higher velocity than the sample stream 1 in the capillary 2. At the end of the capillary 2 mixing occurs of the sample stream 1 and the enveloping flow from the conduit 5, the higher velocity of the enveloping flow causing the particles in the sample stream 1 to be distributed over a greater distance, the sample stream thus being diluted with respect to the particles to be studied. This principle is referred to as hydrodynamic focusing. The dilute sample jet exiting from the nozzle 4 therefore contains the sample particles therefore virtually entirely in singled form. If a focused light beam 7, for example a laser beam, is then directed onto any measuring location 6 in this jet, an individual particle will be observed in the sample stream in almost all cases. Within the scope of the present invention, this principle of hydrodynamic focusing is particularly suitable for singling the particles in the sample.

Figure 2:
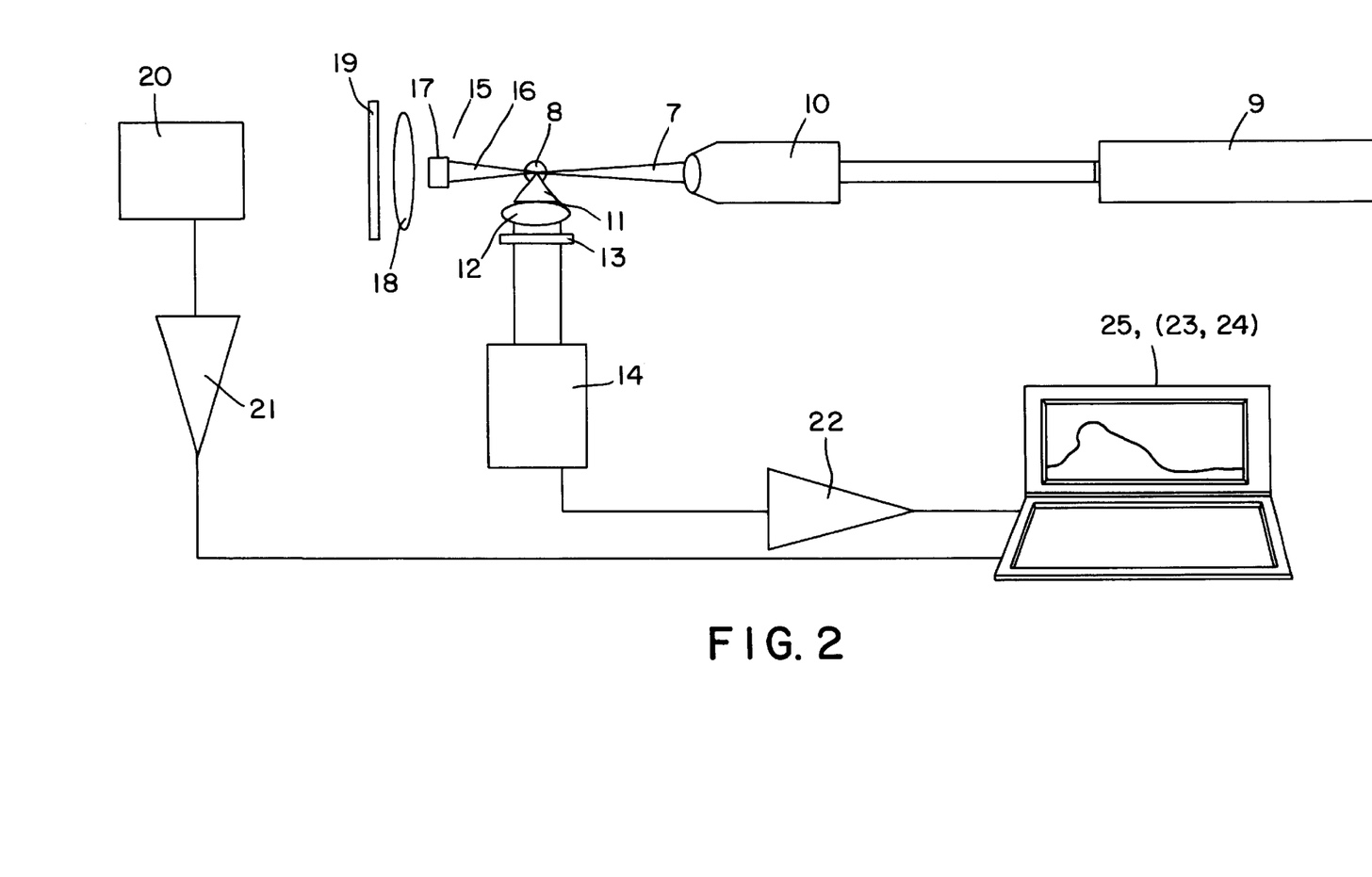
FIG. 2: shows a block diagram of an apparatus for determining the particle size distribution in a sample according to the invention.

FIG. 2 shows a schematic sketch of a measuring setup according to the present invention. A laser 9 supplies excitation light to an objective 10 which focuses the laser light onto a sample 8. In this arrangement the focus is preferably within the sample 8 but may also be outside it, the only essential point being that the intensity of the excitation light in the sample is sufficiently high and that the light cone of excitation light is not so wide as to cause simultaneous excitation of more than one sample particle. A photomultiplier 20 collects, via a lens 18, the excitation light forward-scattered in the sample 8 and transmits the scattered-light intensity values or electrical signals proportional thereto via an amplifier 21 to a computer 25. Interposed before the photomultiplier 20 in this case is a beam stopper 17 and an edge filter 19, the former before and the latter after the lens 18. The function of the beam stopper 17 is to filter out the intense fraction of excitation light passing through without scattering from the cone-shaped scattered-light beam 16 coming from the sample 8. What is filtered out in this arrangement approximates to a core cone having an apex angle of 5°. Apart from that, the measurement of the scattered light is preferably performed in a hollow cone whose inner lateral surface encloses an angle of 5° with the cone axis and whose outer lateral shell encloses an angle of at most 50° with the cone axis. The apparatus according to the invention, according to FIG. 2 suitably has a photomultiplier 14 for recording the fluorescent light 11 from the sample 8. As shown in FIG. 2, the fluorescent light from the sample is preferably recorded in a direction of 90° with respect to the incident light beam. The beam path for recording the fluorescent light additionally includes a lens 12 and an edge filter 13. The photomultiplier 14 passes fluorescent-light intensity signals via an amplifier 22 to the computer 25. This contains one multichannel analyzer 23 and 24 each for the scattered light and for the fluorescent light to sort the intensity values.

Figure 3:
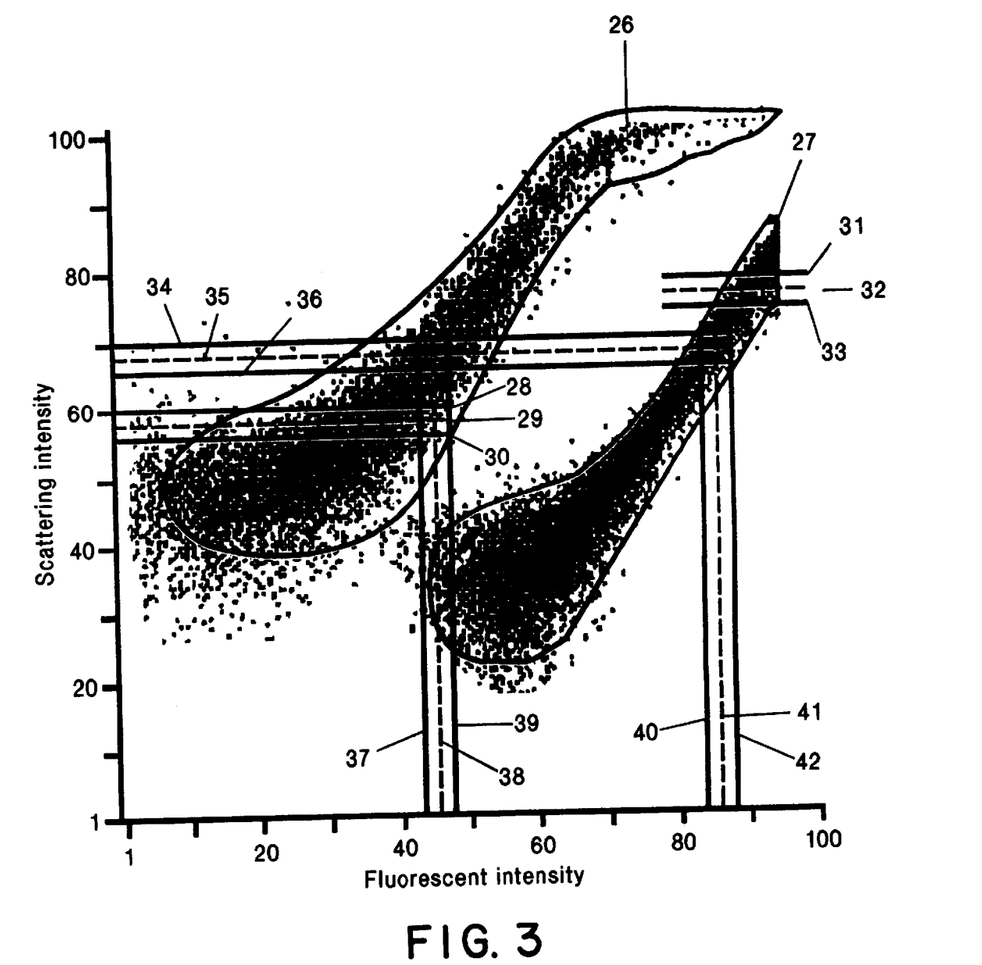
FIG. 3: shows a diagram of the measurement results for the scattered-light intensity and the fluorescent-light intensity in an exemplary measurement involving two particle types in the sample.
Figure 4A:
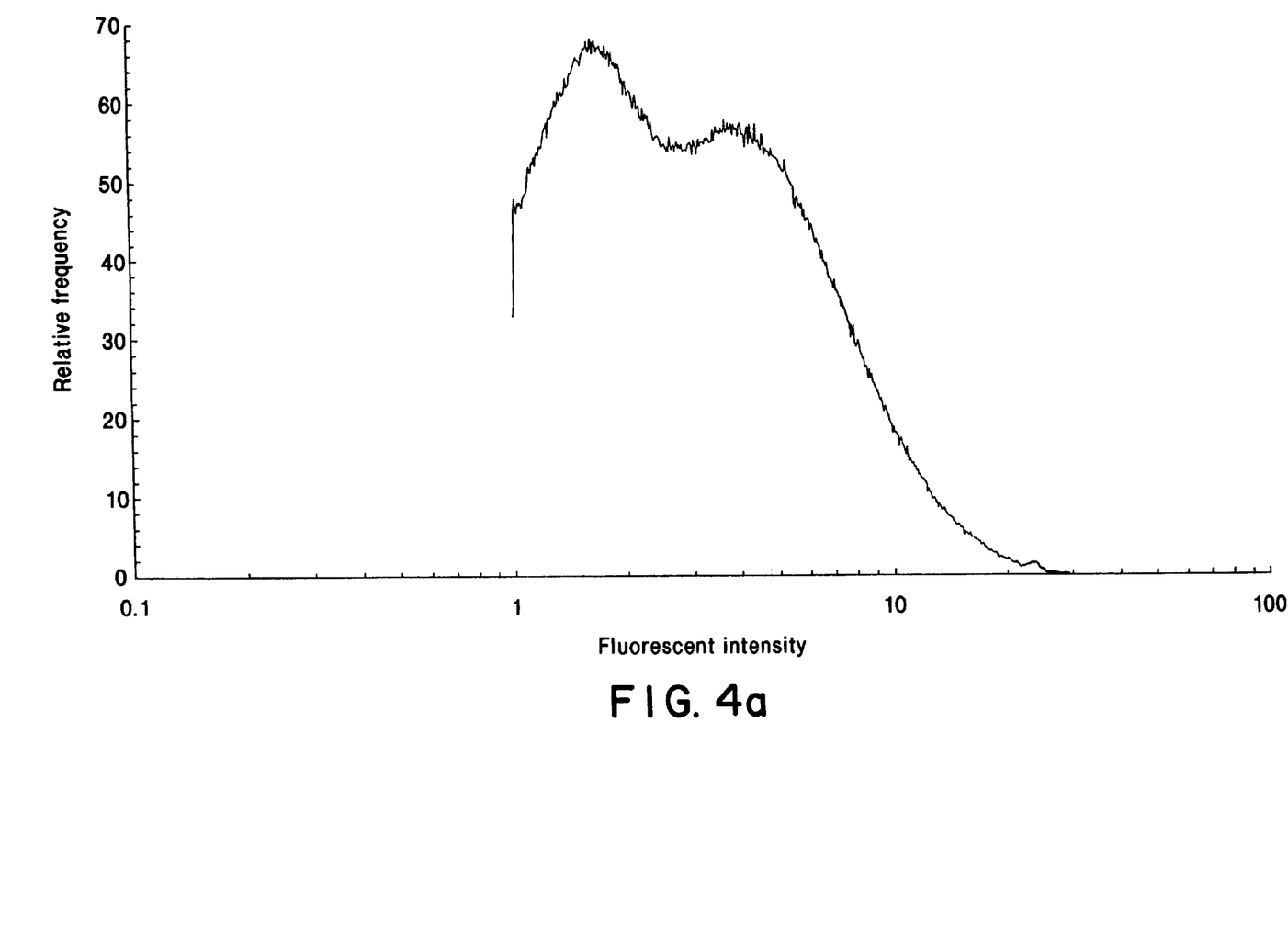
FIG. 4a: shows a diagram of the distribution of the fluorescent-intensity values for the exemplary measurement according to FIG. 3, FIG. 4b: shows a diagram of the relative particle size distribution for the first particle type of the exemplary measurement of FIG. 3, FIG. 4c: shows a diagram of the relative particle size distribution for the second particle type of the exemplary measurement of FIG. 3, FIG. 5: shows a diagram of the joint relative particle size distribution for both particle types of the exemplary measurement of FIG. 3.
Figure 4B:
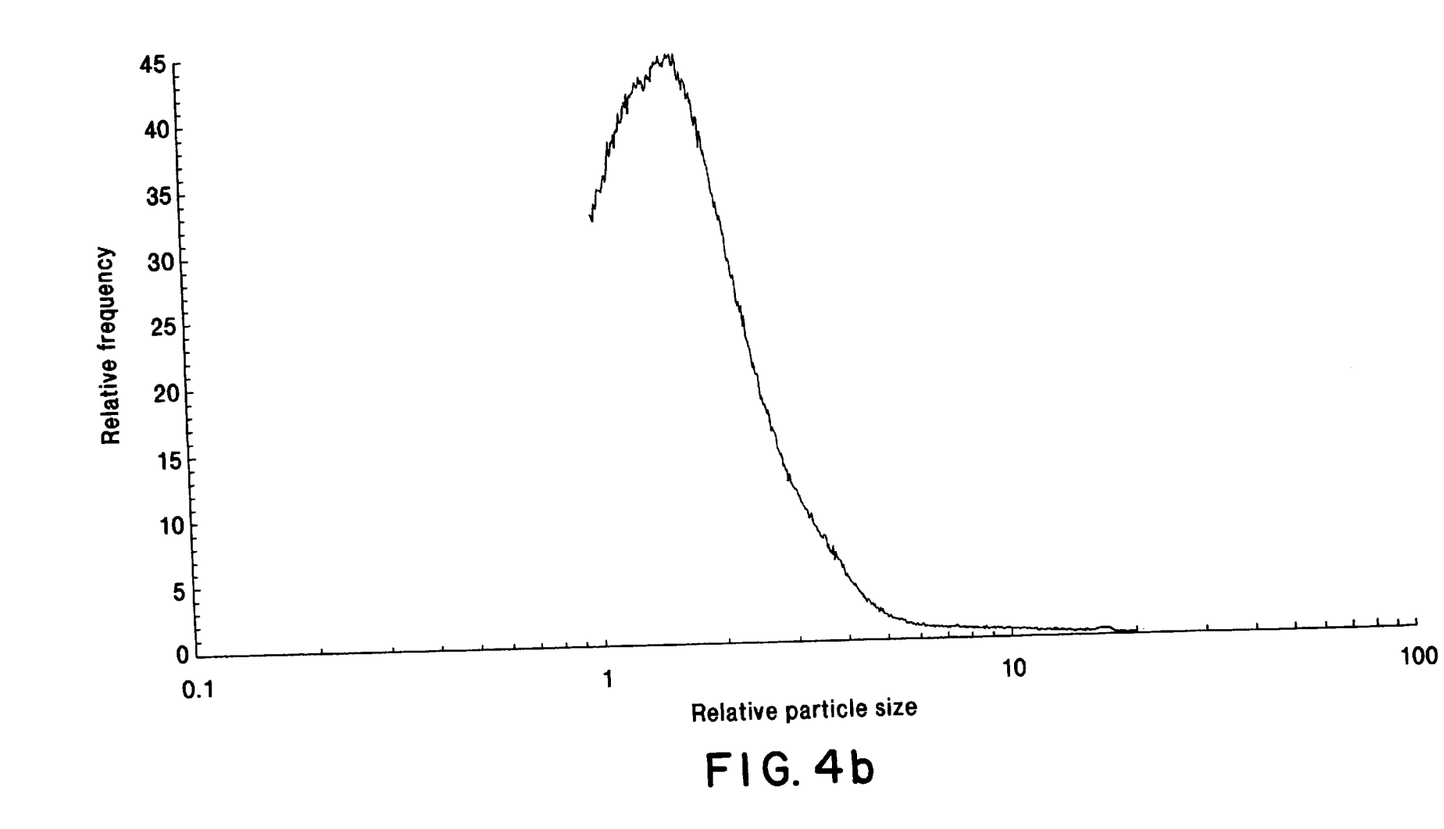
Figure 4C:
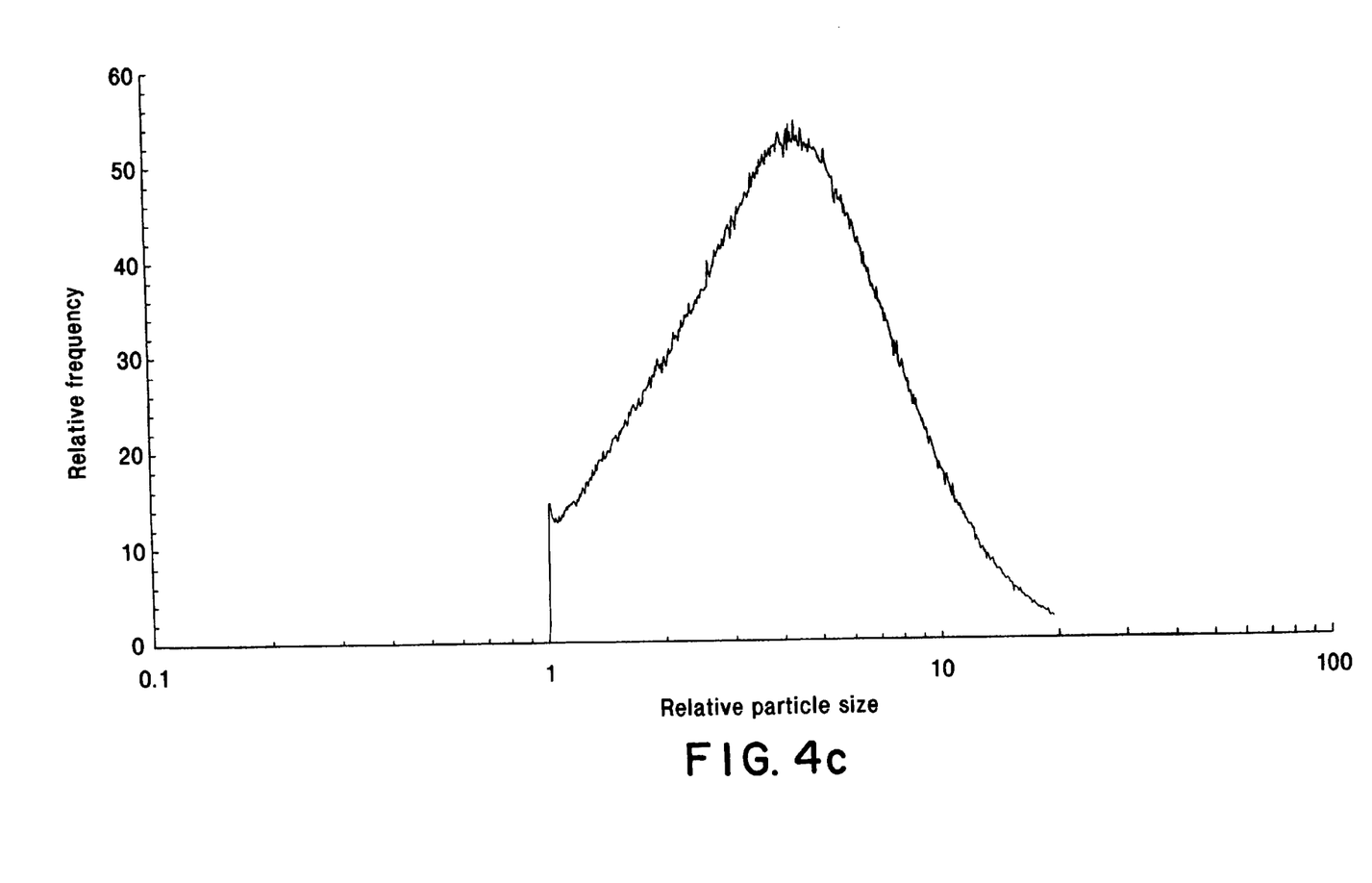
Figure 5:
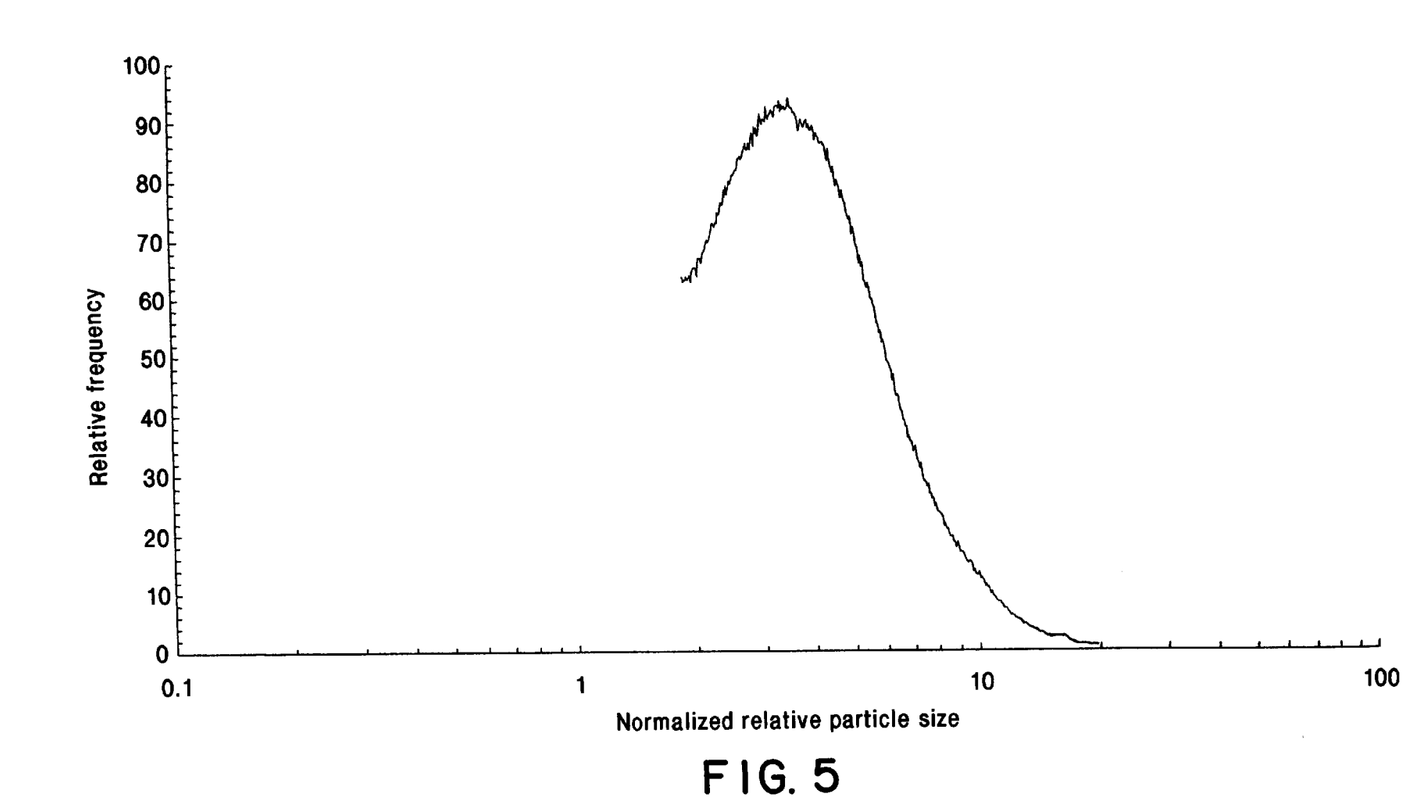

For the exemplary measurement on which the following FIGS. 3 to 5 are based and which makes use of the novel apparatus, a wire water sample was drawn from a paper machine and filtered, so that the hydrophobic contaminant particles were largely separated off. This filtration was carried out with a dynamic drainage jar, in this case a perspex container with a built-in paper wire having a mesh size of 40 μm. This involves the paper slurry first being diluted to a solids content of about 0.4% and then being filtered via the wire with stirring. The filtrate, which contained fibers and contaminant particles having a size less than 40 μm, was then again diluted in a ratio of 1:10 and stained with a dye solution in a ratio of 1:25. This dye solution contained water and 40 mg/l of ethanol and was supersaturated with the commercially available fluorescent dye "Fluorol 555" from BASF, ie. N-(n-butyl)-4-(n-butylamino)naphthalimide. The staining time was about 2 minutes. This ensured that virtually all the hydrophobic contaminant particles were stained, but not the small paper fibers remaining in the filtrate.

Then the stained contaminant particles were filtered from the dye solution and, in an apparatus as described in FIG. 1, hydrodynamically singled in a water jet, the cell used having a diameter of 100 μm and the nozzle a diameter of 200 μm. The enveloping-stream velocity was about 100 times the sample velocity.

Then the singled contaminant particles were studied with a measuring apparatus as described in FIG. 2. The results are depicted in the following FIGS. 3 to 5.

FIG. 3 shows a plot of the measured scattered-light intensity values against the corresponding fluorescent-light intensity values for an exemplary measurement on the above contaminant particles by means of an apparatus according to the invention. The coordinate axes of the diagram of FIG. 3 indicate relative values. It can be seen from FIG. 3 that the pairs of values $(S(P_i),F(P_i))$ for the scattered-light intensity and for the fluorescent-light intensity of the particles $P_i$ arranged themselves into clearly distinguishable experimental-value domains $D_K$ which in this case appear as lobe-shaped domains 26, 27. Each of these domains $D_K$ corresponds to a contaminant, ie. a particle type $T_K$. To exclude erroneous experimental values from further analysis, the experimental-value domains are delimited, in this case shown as continuous lines around the "lobes" 26 and 27. The criterion for drawing the lines around the "lobes" 26, 27, ie. for excluding experimental values in this context may be a strictly mathematical calculations or alternatively the judgement of an experienced experimenter. In the next step, the regions of greatest experimental-value density or greatest experimental-value frequency in the "lobes" 26, 27 are determined and a corresponding scattered-light range $SLR(T_1)$ is selected for the two particle types $T_1$ and $T_2$, in the present case delimited by the lines 28 and 30, and $SLR(T_2)$, in the present case delimited by the lines 31 and 33, these ranges being of predetermined size. Then the two means 29 and 32 of the scattered-light intensity values $S(P_i)$ in the two scattered-light ranges $SLR(T_1)$ and $SLR(T_2)$ are determined. The mean of the two means 29 and 32 is then meant to serve as the mean 35 for the common scattered-light range SLR, in the present case delimited by the lines 34 and 36, which extends symmetrically around the mean 35 and parallel to the coordinate axis of the fluorescence-intensity values. This scattered-light range SLR in turn, like the other defined scattered-light ranges $SLR(T_1)$ and $SLR(T_2)$, is of predetermined size, ie. there is a predetermined difference of the scattered-light intensity value at the upper range limit 34 and the lower range limit 36. In a next step, fluorescent-light ranges $FLR(T_1)$, in the present case delimited by the lines 37 and 39, and $FLR(T_2)$, in the present case delimited by the lines 40 and 42, are determined, the pairs of values $(S(P_i),F(P_i))$ of the fluorescent-light ranges $FLR(T_1)$ and $FLR(T_2)$ also falling into the scattered light range SLR, in the present case delimited by the lines 34 and 36. Then the means $M(FLR(T_1))$, here depicted as line 38, and $M(FLR(T_2))$, here depicted as line 41, of the fluorescent-light intensity values $F(P_i)$ in the two fluorescent-light ranges $FLR(T_1)$ and $FLR(T_2)$ are determined. On the basis of these means, finally, a normalization factor $N(T_2)$ is finally calculated for the particle type $T_2$, $N(T_2)$ being the quotient from $M(FLR(T_2))$ and $M(FLR(T_1))$, the following relationship therefore applying: $N(T_2)=M(FLR(T_2))/M(FLR(T_1))$.

FIG. 3 is, as it were, a two-dimensional projection of the space Sp which is spanned by the scattered-light intensity values $S(P_i)$, the fluorescent-light intensity values $F(P_i)$ and the frequency of the pairs of values $(S(P_i),F(P_i))$. Each of the domains $D_K$ includes at least one local maximum of the pairs-of-values frequency and consequently of the pairs-of-values density for the corresponding particle type $T_K$. Rather than by the type of analysis described, the "lobes" can also be analyzed differently, for example by their parallel spacing being determined in the diagram according to FIG. 3 or by any other algorithm, as long as it takes adequate account of the physical conditions relating to the measurement.

FIG. 4a shows the frequency of the fluorescence-intensity values for the exemplary measurement discussed in FIG. 3, for both particle types $T_1$ and $T_2$. Owing to the different stainability and quantum yield of the different particle types $T_1$ and $T_2$ this cannot be used as a basis for reliable information on the joint particle size distribution of the different sample particles.

FIGS. 4b and 4c show the relative particle size distributions (in arbitrary units), which are obtained for the particle types $T_1$ and $T_2$, after these have been separated, via the assignment shown in FIG. 3 to an experimental-value range, ie. a "lobe".

FIG. 5, finally, shows the result of the method according to the invention, the particle type-independent particle size distribution which is obtained by normalization of the relative particle size distribution of the particle type $T_2$ to the relative particle size distribution of the particle type $T_1$ using the normalization factor $N(T_2)$. FIG. 5 depicts a joint relative particle size distribution, ie. a normalized relative particle size distribution. Alternatively, however, a joint absolute particle size distribution can be calculated if at least one of the two relative particle size distributions for the different particle types $T_1$, $T_2$ is calibrated for absolute particle sizes.

The present invention therefore provides a method and an apparatus for determining the relative and absolute particle size distribution of different particles in a sample, which method is simple and rapid and therefore particularly suitable for on-line operation.

We claim:

1. A method for determining the size distribution of at least two particle types ($T_K$) of fluorescent particles (Pi) in a sample, which comprises
   (i) flowing the sample in a stream of singled out particles through a focused light beam, (ii) measuring, for each singled out particle moving through the light beam,
   (a) at least one scattered-light intensity value ($S(P_i)$), and
   (b) at least one fluorescent-light intensity value ($F(P_i)$)
(iii) plotting the scattered-light-intensity value against the corresponding fluorescent-light intensity for each of the singled out particles whereby each of the at least two particle types arrange themselves into domains ($D_K$), each determining a particle type ($T_K$),
(iv) calculating a relative particle size distribution for each individual particle type ($T_k$)
(v) normalizing the relative particle size distribution for the individual particle types forming a joint relative particle size distribution of the at least two particle types with respect to one another.

2. The method of claim 1 wherein stream of singled out particles is formed by hydrodynamic focusing.

3. The method of claim 1 wherein the beam of light is from a coherent light source.

4. The method of claim 1 wherein the particles are hydrophopic.

5. The method of claim 4 wherein the sample is a wire water sample drawn from a paper machine and filtered, so that the hydrophobic contaminant particles are essentially separated off.

6. The method of claim 5 wherein the particles ($P_i$) are tagged by at least one fluorescent dye.

7. The method of claim 5 wherein the at least one fluorescent dye is lipophilic.

8. An apparatus for determining the size distribution of at least two particle types ($T_K$) of fluorescent particles (Pi) in a sample, which comprises
   (i) means for flowing the sample in a stream of singled out particles through a focused beam of light,
   (ii) means for measuring, for each singled out particle moving through the light beam,
      (a) at least one scattered-light intensity value ($S(P_i)$), and
      (b) at least one fluorescent-light intensity value ($F(P_i)$)
   (iii) means for plotting the scattered-light intensity value against the corresponding fluorescent-light intensity for each of the singled out particles whereby each of the at least two particle types arrange themselves into domains ($D_K$), each determining a particle type ($T_K$),
   (iv) means for calculating a relative particle size distribution for each individual particle type ($T_k$)
   (v) means for normalizing the relative particle size distributions for the individual particle types forming a joint relative particle size with respect to one another distribution of the at least two particle types.

9. The apparatus of claim 8 wherein the means for forming the stream of singled out particles employs hydrodynamic focusing.

10. The apparatus of claim 8 wherein the source for the beam of light is a laser.

* * * * *